US00PP20098P2

(12) United States Plant Patent
Giesen

(10) Patent No.: US PP20,098 P2
(45) Date of Patent: Jun. 16, 2009

(54) ***DIASCIA* PLANT NAMED 'DALA ROS08'**

(50) Latin Name: *Diascia barberae*
Varietal Denomination: Dala Ros08

(75) Inventor: Eric Giesen, Andijk (NL)

(73) Assignee: Goldsmith Seeds Europe B.V., Andijk (NL)

( * ) Notice: Subject to any disclaimer, the term of this patent is extended or adjusted under 35 U.S.C. 154(b) by 0 days.

(21) Appl. No.: 12/150,463

(22) Filed: Apr. 28, 2008

(51) Int. Cl.
*A01H 5/00* (2006.01)

(52) U.S. Cl. ..... Plt./425
(58) Field of Classification Search ..... Plt./425
See application file for complete search history.

*Primary Examiner*—Annette H Para
(74) *Attorney, Agent, or Firm*—C. A. Whealy

(57) ABSTRACT

A new and distinct cultivar of *Diascia* plant named 'Dala Ros08', characterized by its dense and bushy, rounded, spreading to semi-trailing plant habit; freely branching habit; freely flowering habit; dark pink-colored flowers; and good garden performance.

1 Drawing Sheet

Botanical designation: *Diascia barberae.*
Cultivar denomination: 'Dala Ros08'.

BACKGROUND OF THE INVENTION

The present invention relates to a new and distinct cultivar of *Diascia,* botanically known as *Diascia barberae,* and hereinafter referred to by the name 'Dala Ros08'.

The new *Diascia* is a product of a planned breeding program conducted by the Inventor in Andijk, The Netherlands. The objective of the breeding program is to create new freely-flowering *Diascia* cultivars with uniform plant habit and attractive flower colors.

The new *Diascia* originated from a cross-pollination made by the Inventor in Andijk, The Netherlands in January, 2004 of a proprietary selection of *Diascia barberae* identified as code number DS03-98-1, not patented, as the female, or seed, parent with a proprietary selection of *Diascia barberae* identified as code number DS04-41-1, not patented, as the male, or pollen, parent. Seeds resulting from the crossing were sown in March, 2004. The new cultivar *Diascia* was discovered and selected by the Inventor as a flowering plant within the progeny of the stated cross-pollination in a controlled greenhouse environment in Andijk, The Netherlands in July, 2004.

Asexual reproduction of the new *Diascia* by terminal cuttings in a controlled greenhouse environment in Andijk, The Netherlands since July, 2004, has shown that the unique features of this new *Diascia* are stable and reproduced true to type in successive generations.

SUMMARY OF THE INVENTION

Plants of the new *Diascia* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Dala Ros08'. These characteristics in combination distinguish 'Dala Ros08' as a new and distinct cultivar of *Diascia:*

1. Dense and bushy, rounded, spreading to semi-trailing plant habit.
2. Freely branching habit.
3. Freely flowering habit.
4. Dark pink-colored flowers.
5. Good garden performance.

Plants of the new *Diascia* can be compared to plants of the female parent selection. Plants of the new *Diascia* differ from plants of the female parent selection in the following characteristics:

1. Plants of the new *Diascia* have longer internodes and longer peduncles than plants of the female parent selection.
2. Plants of the new *Diascia* are more freely flowering than plants of the female parent selection.
3. Plants of the new *Diascia* have larger flowers than plants of the female parent selection.
4. Plants of the new *Diascia* have darker pink-colored flowers than plants of the female parent selection.

Plants of the new *Diascia* can be compared to plants of the male parent selection. Plants of the new *Diascia* differ from plants of the male parent selection in the following characteristics:

1. Plants of the new *Diascia* are more upright than plants of the male parent selection.
2. Plants of the new *Diascia* are larger and more dense than plants of the male parent selection.
3. Plants of the new *Diascia* have more intense pink-colored flowers than plants of the male parent selection.

Plants of the new *Diascia* can be compared to plants of the *Diascia barberae* 'Dala Rossa', disclosed in U.S. Plant Pat. No. 17,200. In side-by-side comparisons conducted in Andijk, The Netherlands, plants of the new *Diascia* differed from plants of 'Dala Rossa' in the following characteristics:

1. Plants of the new *Diascia* were denser and fuller than plants of 'Dala Rossa'.
2. Plants of the new *Diascia* were more freely flowering than plants of 'Dala Rossa'.
3. Plants of the new *Diascia* had larger flowers than plants of 'Dala Rossa'.

BRIEF DESCRIPTION OF THE PHOTOGRAPH

The accompanying colored photograph illustrates the overall appearance of the new *Diascia,* showing the colors as true as it is reasonably possible to obtain in colored reproductions of this type. Colors in the photograph may differ slightly from the color values cited in the detailed botanical description which accurately describe the colors of the new *Diascia.* The photograph comprises a close-up view of a typical flowering plant of 'Dala Ros08' grown in a container. Plants used for the photograph were grown in Gilroy, Calif. during the summer and autumn in an outdoor nursery and cultural conditions typical of *Diascia* production. Plants were six months old when the photograph was taken.

DETAILED BOTANICAL DESCRIPTION

The following observations, measurements and values describe plants grown in Hillscheid, Germany in 15-cm containers in a greenhouse during the spring and under conditions which closely approximate commercial production. Plants were pinched one time and were three months old when the description was taken. In the description, color references are made to The Royal Horticultural Society Colour Chart, 2001 Edition, except where general terms of ordinary dictionary significance are used.

Botanical classification: *Diascia barberae* 'Dala Ros08'.

Parentage:

*Female, or seed, parent.*—Proprietary selection of *Diascia barberae* identified as code number DS03-98-1, not patented.

*Male or pollen parent.*—Proprietary selection of *Diascia barberae* identified as code number DS04-41-1, not patented.

Propagation:

*Type.*—By vegetative cuttings.

*Time to initiate and develop roots.*—About 16 to 20 days.

*Root description.*—Fibrous; white in color.

*Rooting habit.*—Freely branching.

Plant description:

*Plant form and growth habit.*—Dense and bushy, rounded, spreading to semi-trailing plant habit.

*Branching habit.*—Freely branching habit; when pinched, lateral branches potentially develop at every node.

*Plant height.*—About 26 cm.

*Plant diameter* (*area of spread*).—About 60 cm.

Lateral branch description:

*Length.*—About 30 cm to 35 cm.

*Diameter.*—About 2 mm to 3 mm.

*Internode length.*—About 2.5 cm to 4 cm.

*Texture.*—Sparsely pubescent.

*Color.*—Close to 144B.

Foliage description:

*Arrangement.*—Decussate, simple.

*Length.*—About 2.2 cm to 3 cm.

*Width.*—About 1.7 cm to 2.5 cm.

*Shape.*—Cordate.

*Apex.*—Obtuse.

*Base.*—Cordate.

*Margin.*—Weakly crenate.

*Texture, upper and lower surfaces.*—Smooth, glabrous.

*Venation pattern.*—Developing foliage, palmate; fully expanded foliage, pinnate.

*Color.*—Developing foliage, upper surface: Close to 143B. Developing foliage, lower surface: Close to 144B. Fully expanded foliage, upper surface: Between 137D and 143A; venation, close to 144B. Fully expanded foliage, lower surface: Close to 138B; venation, close to 144B.

*Petiole.*—Length: About 1 mm to 3 mm. Diameter: About 1 mm to 2 mm. Texture, upper and lower surfaces: Smooth, glabrous. Color, upper and lower surfaces: Close to 144A.

Flower description:

*Flower arrangement.*—Single flowers arranged on terminal racemes in an alternate arrangement; zygomorphic with five lobes fused at the base. Freely flowering habit with usually about 15 open flowers and flower buds per raceme; about 60 to 110 racemes develop per plant. Flowers face upright and outwardly. Flowers not fragrant.

*Natural flowering season.*—Plants flower freely and continuously from the spring into the fall in Germany. Flowers last about three to four days on the plant. Flowers not persistent.

*Inflorescence height.*—About 10 cm to 12 cm.

*Flower diameter.*—About 2 cm to 2.2 cm.

*Flower height.*—About 2.1 cm to 2.3 cm.

*Flower depth.*—About 5 mm.

*Flower bud.*—Length: About 7 mm. Diameter: About 1 cm. Shape: Conical with rounded base. Color: Close to 69A; towards the edges, close to 68A.

*Corolla.*—Arrangement: Corolla consists of five petals modified into two banner petals, two lateral petals with spurs and a protruding lip petal. Corolla tube length: About 1.5 cm to 1.7 cm. Banner lobe length: About 5 mm. Banner lobe width: About 6 mm. Lateral lobe length: About 6 mm. Lateral lobe width: About 7 mm. Lower lobe length: About 1 cm to 1.1 cm. Lower lobe width: About 1.4 cm to 1.5 cm. Banner, lateral and lower lobe shape: Orbicular. Banner, lateral and lower lobe apex: Rounded. Banner, lateral and lower lobe margin: Entire. Banner, lateral and lower lobe texture, upper and lower surfaces: Smooth, glabrous. Spur length: About 6 mm. Spur diameter: About 3 mm. Spur orientation: Curved downward. Banner, lateral and lower lobe color: When opening, upper surface: Close to 68A. When opening, lower surface: Close to 70D. Fully developed, upper surface: Close to 67B to 67C; towards the base of the banner lobes, patch of close to 12A. Fully developed, lower surface: Between 67C to 68A. Corolla tube, inside: Close to 60C to 60D. Corolla tube, outside: Close to 11A; fine lines, close to 162B. Spur: Close to 70B.

*Sepals.*—Appearance: Five sepals fused into a star-shaped calyx. Length: About 2.5 mm. Width: About 1 mm. Shape: Lanceolate. Apex: Acute. Margin: Entire. Texture, upper and lower surfaces: Densely hirsute; rough. Color, upper and lower surfaces: Close to 137D.

*Peduncles.*—Length: About 9 cm to 11 cm. Diameter: About 2 mm. Texture: Hirsute. Color: Close to 143A to 143B.

*Pedicels.*—Length: About 2 cm. Diameter: About 2 mm. Texture: Finely pubescent. Color: Close to 137D tinted with 147A.

*Reproductive organs.*—Androecium: Stamen number per flower: About four. Filament length: About 3 mm Filament diameter: About 1 mm. Filament color: Close to 70B. Anther shape: Ovoid. Anther length: Less than 1 mm. Anther color: Close to 14D. Amount of pollen: Abundant. Pollen color: Close to 12A. Gynoecium: Pistil number per flower: One. Pistil length: About 4 mm. Style color: Close to 145B. Stigma color: Close to 144A.

*Seed/fruit.*—Seed and fruit production have not been observed.

Garden performance: Plants of the new *Diascia* have been observed to have good garden performance and tolerate rain, wind and a wide range of temperatures.

Pathogen/pest resistance: Plants of the new *Diascia* have not been shown to be resistant to pathogens and pests common to *Diascia.*

It is claimed:

1. A new and distinct *Diascia* plant named 'Dala Ros08' as illustrated and described.

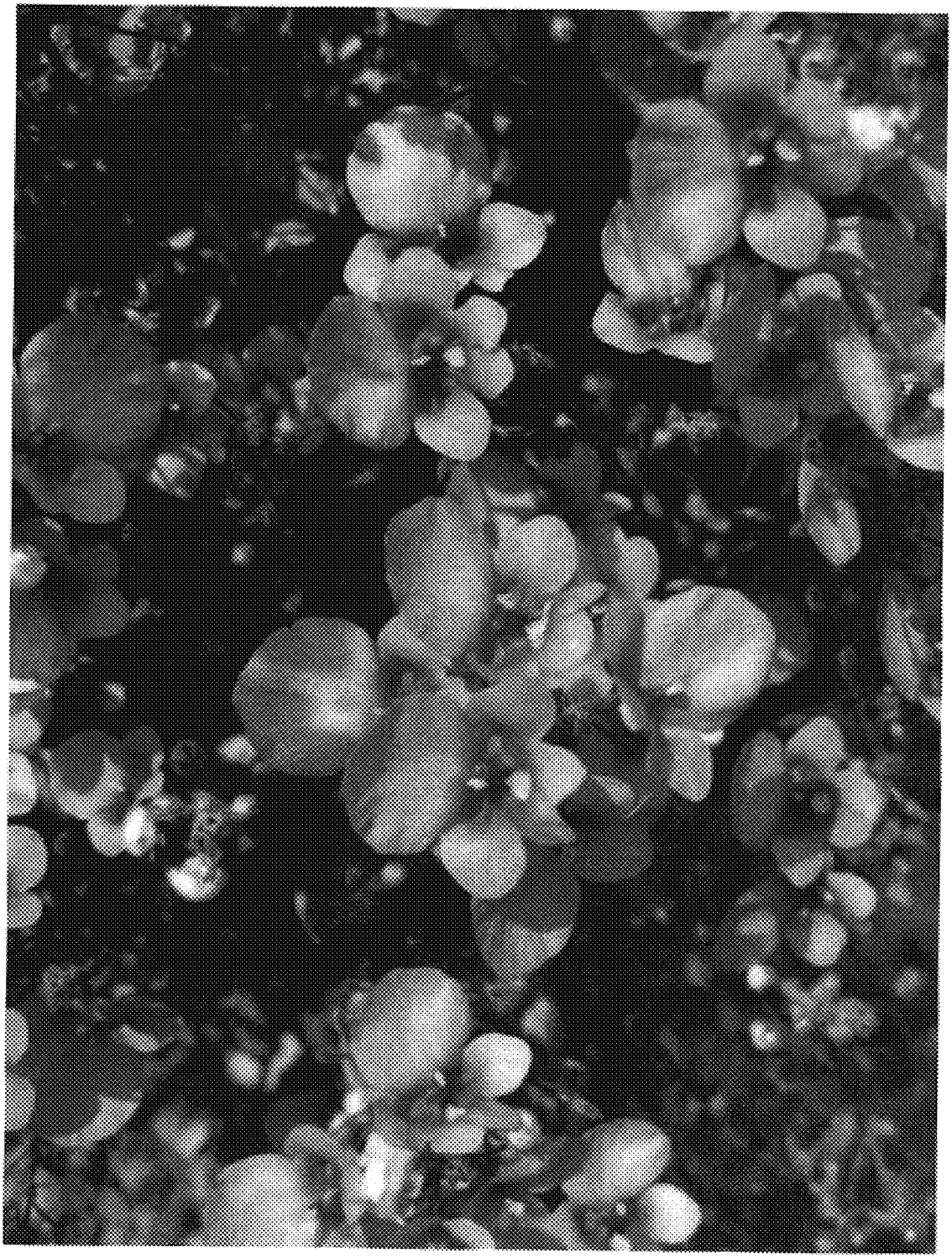

* * * * *